US 6,704,104 B2

(12) United States Patent
Li

(10) Patent No.: US 6,704,104 B2
(45) Date of Patent: Mar. 9, 2004

(54) MULTI-WAVELENGTH ARRAY READER FOR BIOLOGICAL ASSAY

(75) Inventor: Qingbo Li, State College, PA (US)

(73) Assignee: Spectrumedix LLC, State College, PA (US)

(*) Notice: Subject to any disclaimer, the term of this patent is extended or adjusted under 35 U.S.C. 154(b) by 0 days.

(21) Appl. No.: 10/221,734
(22) PCT Filed: Mar. 15, 2001
(86) PCT No.: PCT/US01/08527
§ 371 (c)(1), (2), (4) Date: Sep. 16, 2002
(87) PCT Pub. No.: WO01/69211
PCT Pub. Date: Sep. 20, 2001

(65) Prior Publication Data
US 2003/0223059 A1 Dec. 4, 2003

Related U.S. Application Data
(60) Provisional application No. 60/189,889, filed on Mar. 16, 2000.

(51) Int. Cl.⁷ .............................................. G01N 21/64
(52) U.S. Cl. ..................... 356/317; 356/318; 250/458.1
(58) Field of Search ................................. 356/317, 318; 250/458.1, 459.1, 461.1, 461.2

(56) References Cited

U.S. PATENT DOCUMENTS

| 5,780,231 A | 7/1998 | Brenner |
| 5,998,796 A | 12/1999 | Liu et al. |
| 6,118,127 A | 9/2000 | Liu et al. |

Primary Examiner—F. L. Evans

(57) ABSTRACT

The present invention relates to an array reader having a light source configured to emit an excitation light, a substrate comprising a plurality of sites spatially configured as a two-dimensional array having a plurality of rows and a plurality of columns, where each site is configured to support a sample. The array reader includes a changing device configured to determine which of said plurality of sites is illuminated at any given instant and a detector comprising a two-dimensional array of light sensitive elements, transmission grating beam splitter (TGBS) disposed along an optical path between the substrate and the detector, and a single light focusing element disposed along an optical path between the substrate and the detector. The TGBS is configured to receive non-collimated light emitted by at least one sample illuminated by said excitation light.

25 Claims, 16 Drawing Sheets

MULTI-WAVELENGTH ARRAY READER FOR BIOLOGICAL ASSAY

RELATED APPLICATIONS

This application claims priority to provisional application No. 60/189,889, filed Mar. 16, 2000, and entitled "Multi-Wavelength Array Reader for Biological Assay" which is incorporated herein in its entirety.

Furthermore, this application is related to U.S. applications (1)Ser. No. 09/413,355, filed Oct. 6, 1999, entitled "Uniform Laser Excitation and Detection in Capillary Array Electrophoresis System and Method"; and (2) Ser. No. 09/676,526, filed Oct. 2, 2000, entitled "Electrophoretic Analysis System Having In-Situ Calibration".

TECHNICAL FIELD

This invention relates to a detector system for performing sample analysis, such as DNA sequencing, DNA fingerprinting, gene expression analysis, and the like. More particularly, it pertains to a detector system which employs a transmission grating beam splitter for separating incoming light, either fluoresced or otherwise emitted from samples separated from one another in a two-dimensional array, into multiple order diffraction bands and wavelengths.

BACKGROUND

Genetic sequence information, such as that obtained in the Human Genome Project, has applications in functional genomic research, disease diagnostics, drug discovery, and the like. Micro-array technologies have arisen to meet the demand for expanding the acquisition and utilization of the genetic information. These technologies often involve imaging a microfabricated array of probe sequences disposed on a support, such as a microchip, slide, array or chip. For example, genetic mutations may be detected by a method known as sequencing by hybridization. In sequencing by hybridization, a solution containing one or more targets to be sequenced (i.e., samples from patients) contacts multiple DNA probes arranged in a microfabricated array. The targets will bind or hybridize with probes in the array that contain complementary sequences. Generally, the targets are labeled with a fluorescent marker, radioactive isotopes, enzymes, or other types of markers. Accordingly, locations at which targets hybridize with complimentary probes can be identified by locating the markers. Based on the locations where hybridization occur, information regarding the target sequences can be extracted. The existence of a mutation may be determined by comparing the target sequence with the wild type.

Microchip fabrication technology has recently entered the commercialization stage in which multiple vendors provide robotic microchip printing devices for users to customize their own chips for specific studies, including gene expression, genotyping, sequencing, and the like. The printing devices generate two-dimensional arrays of spots or analysis sites. A site refers to an area or region of a substrate that accommodates a fluorophore or is functionalized to provide a response indicative of the amount of a target substance present in a sample. Typically, different sites are functionalized to provide a response indicative of different targets. To improve precision, however, more than one site can be functionalized to respond to the same target. Preferably, the sites are arranged as an array of discrete spots, with each spot being hybridized with one or more different probes.

Stand-alone array printers can be purchased separately for less than about $5000. These printing devices can automatically print hundreds of chips, or slides, per load. The typical spot size printed on a chip is about 20–100 $\mu$m. Typically, the spots are printed with strands of DNA, antibodies, or the like, configured to indicate the presence of or amount of a particular target present in a sample. Spot sizes of tens of microns or more generate relatively low density microchips. Low-density microchips, however, are more practical when researchers have identified a limited set of targets, such as a specific groups of genes, they wish to study or use as diagnostic markers. More difficult diagnostic and research assays, in contrast, require higher density arrays at least in part because less information is known about the sample prior to the analysis. Higher density arrays of the type required for these analyses are produced by, for example, Affymetrix using lithographic techniques. In some cases, feature sites may be as small as a few microns or even a single molecule. For example, about $10^5$ to $10^6$ features may be fabricated in an area of only 12.8 mm$^2$.

Because of their smaller spot size and more compact architecture, the high density arrays require high resolution optical devices or readers to interrogate the sites of the arrays. Several vendors have manufactured microchip reading devices to detect the signals from these chips. Currently, all these devices are based on fluorescence detection, which is the detection of fluoresced light resulting from one or more fluorophores upon exposure of the fluorophores to an excitation light. They employ either confocal scanners combined with photomultiplier tube (PMT) detectors (for companies such as Genetic MicroSystems, GSI Lumonics, Virtek Vision), or a CCD detector with an imaging lens (Hitachi). These devices can detect two dyes, such as Cy3 and CyS, by alternating the excitation laser wavelength to match a specific dye excitation spectral maximum, and/or switching an optical filter to match the fluorescent spectrum of a particular dye. Neither of these devices has a spectrometer capable of simultaneous multi-wavelength detection to simultaneously distinguish multiple dyes from sites within an array. Additionally, confocal scanners require precisely controlled movement of either the scanner head or the chip in three dimensions, which compromise the robustness of the instrument.

Determining the presence of multiple fluorophores within an array has biologically important applications. For example, the probe arrays may be designed specifically to detect genetic diseases, either from acquired or inherited mutations in an individual DNA. These include genetic diseases such as cystic fibrosis, diabetes, and muscular dystrophy, as well as acquired diseases such as cancer. Microchip arrays have proved to be a high-throughput method for gene expression studies, capable of screening thousands of genes on a single microchip. In order to extract the meaningful information from such large amount of gene expression data from one biological sample, one has to compare it to a reference sample in order to obtain the differential expression pattern. The reproducibility of the response obtained from individual sites in an array of sites is influenced by a number of experimental factors, such as temperature, the hybridization buffer, the quality of the substrate, the ability to print arrays with precise amounts of material within each site and the like. One way to eliminate uncertainties introduced by these site-to-site variations is to simultaneously measure the response of both the sample and the control for each site. Measuring both a sample and control response from each site, however, requires that the fluorescent detection system be able to distinguish the sample and control responses rapidly and efficiently.

Another demanding example that would require the ability to distinguish multiple responses is the use of microfabricated arrays to monitor changes in gene expression patterns of a cell line during different phases of a drug treatment study. It would be desirable to monitor the gene expression at many points in time, such as five or more times, during the study. Because these gene expression changes can be subtle, a highly sensitive and precise monitoring method is required. If the samples obtained from different phases of the drug treatment are analyzed within different sites in an array, however, the above-mentioned variations in the site to site response can decrease the precision of the measured response, which decreases the value of the information to the researcher or clinician. In order to reduce the experimental variation, the samples from different points during the study would desirably be pooled together and analyzed within the same sites on the array. In general, if N samples were pooled together in a particular site, the number of fluorophores in the site would range from zero to N depending on how many of the samples contain a target having an affinity for a probe disposed at that site. Therefore, the multiplexed sample approach requires a detection system able to distinguish simultaneously the response from as many as N different fluorophores to maximize the sample analysis rate (throughput).

Systems that utilize interchangeable filters or different excitation wavelengths to sequentially measure the response of different fluorophores, have reduced throughput because they cannot simultaneously measure the response from multiple dyes. Moreover, the source light used to excite the fluorescence may photobleach fluorophores in the sample. Therefore, the response of a fluorophore that is measured later in the measuring sequence may be biased lower by the photobleaching.

Therefore, there is a need to simultaneously measure the response of multiple fluorophores from each site within an array. The present invention involves using a spectrometer to spectrally obtain simultaneously the total fluorescence spectrum resulting from multiple fluorophores. Based on the total observed fluorescence spectrum, deconvolution techniques can be used to resolve the amount of multiple individual fluorophores in the sample. Within a given spectral range, deconvolution techniques allow more fluorophores to be resolved than by using filters. Therefore, more samples can be multiplexed within each site of the array to increase throughput and accuracy of differential gene expression measurements. Multiplexing a group of spectrally close dyes allows more efficient excitation using a single excitation source. Wavelength selection using a transmission grating eliminates the need for switching filters, simplifies instrumental design, and increases fluorescence light collection efficiency. The present invention offers significant advantages over the method of using different wavelength lasers to selectively excite each individual dye coupled with narrow band pass filters for selective detection of the dye.

SUMMARY OF THE INVENTION

An embodiment of the present invention relates to an array reader comprising a light source configured to emit an excitation light and a substrate having a plurality of discrete sites arranged in at least two dimensions. Each site is configured to support a sample. The array reader includes a detector comprising an array of light sensitive elements and a diffracting element disposed along an optical path between the substrate and the detector. The diffracting element is configured to receive non-collimated light emitted by at least one sample illuminated by said excitation light.

Each site may have associated therewith one or more sequences of nucleotides, proteins or peptides serving as probes. The probes may be integrally bound to substrate.

The substrate can comprise a platform, a microchip, slide, or a microtitre tray having a plurality of wells configured to accommodate samples.

The diffracting element is preferably a transmission grating beam splitter (TGBS). The TGBS separates the non-collimated light received from the at least one sample into a $0^{th}$-order component which is received by a first set of said light sensitive elements and a higher-order component which is received by a second set of said light sensitive elements, the second set being spaced apart from the first set. Each member of the second set is disposed at a distance from the first set which is indicative of a wavelength of light received by that member.

In another embodiment, the non-collimated light is received by the TGBS without first having been optically altered by a light focusing element. A single light focusing element is disposed along an optical path segment between the TGBS and the detector.

In yet another embodiment, the array reader comprises a single light focusing element disposed along the optical path between the substrate and the detector, said light focusing element being disposed between the substrate and the TGBS.

The substrate preferably comprises a two-dimensional array of sites arranged as a plurality of rows and a plurality of columns. In one embodiment, the array reader comprises a changing device configured to determine which of said plurality of sites is illuminated at any given instant. The changing device can be configured to alter a position of the sites with respect to the detector. Alternatively, or in combination with this embodiment, the changing device is configured to alter a direction of the excitation light so as to selectively illuminate a subset of said plurality of sites.

Yet another embodiment of the present invention relates to an array reader comprising a light source configured to emit an excitation light, a substrate comprising a plurality of sites spatially configured as a two-dimensional array having a plurality of rows and a plurality of columns, each site configured to support a sample, a changing device configured to determine which of said plurality of sites is illuminated at any given instant, a detector comprising a two-dimensional array of light sensitive elements, a transmission grating beam splitter(TGBS)disposed along an optical path between the substrate and the detector, a single light focusing element disposed along an optical path between the substrate and the detector, wherein the TGBS is configured to receive non-collimated light emitted by at least one sample illuminated by said excitation light, the non-collimated light being received by the TGBS without first having been optically altered by a light focusing element.

BRIEF DESCRIPTION OF THE DRAWINGS

The present invention is described in detail below with reference to the drawings in which.

DETAILED DESCRIPTION OF THE PREFERRED EMBODIMENT

Figure 1:
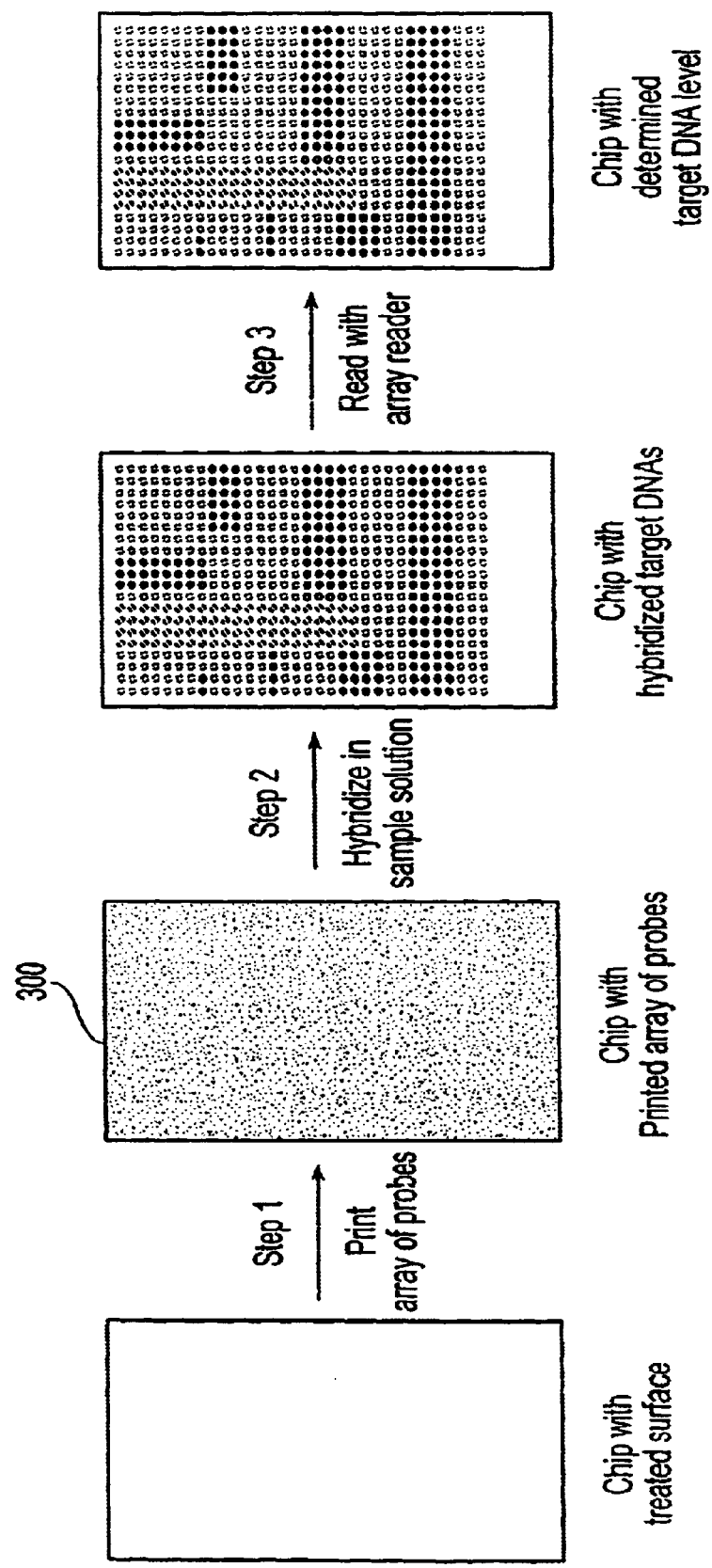
FIG. 1 shows a substrate supporting an array of sites according to the invention.

The contents of aforementioned U.S. patent application Ser. Nos. 09/413,355 and 09/676,526, and U.S. Pat. No. 6,118,127 are incorporated by reference to the extent necessary to understand the present invention.

The present invention relates to an array reader configured to measure fluorescence from an array of sites arranged in at least two dimensions.

Arrays of Sites

Each site of an array of sites is preferably configured to accommodate a fluorophore containing sample. The sample can be a fluid, a solid, or a liquid. Each site is preferably supported by a substrate. The substrate can be composed from a wide range of materials, either biological, non-biological, organic, inorganic, or a combination of any of these. The substrate may be configured with discrete particles, strands, precipitates, gels, sheets, tubing, spheres, containers, capillaries, pads, slices, films, plates, slides, and the like. Substrates are preferably substantially flat but may take on a variety of alternative surface configurations. Thus, the substrate may have any convenient shape, such as a disc, square, sphere, circle, cube, etc. Substrates suitable for use with the present invention are sometimes referred to in the art as microchips, chips, or arrays.

The substrate is chosen to provide appropriate optical characteristics, such as a low background fluorescence. Preferred materials include glass, quartz, and fused silica, which produce sufficiently low fluorescence. Alternatively, the substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof.

Surfaces on the solid substrate will usually, though not always, be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si-OH functionalities, such as those found on silica surfaces.

The substrate or the substrate and its surface generally support an array of assay sites. For example, a preferred substrate comprises a microtitre tray having a plurality of wells configured to accommodate fluorophore-containing samples. Each well corresponds to an assay site. The wells can be of any size or shape suited for containing an amount of sample sufficient to obtain fluorescence therefrom. The wells can be arranged as a regular array of rows and columns or in other patterns such as a honeycomb pattern or irregular patterns.

The substrate used with the apparatus of the invention can comprise a platform. Preferably, the platform is configured to releasably secure the substrate at a desired analysis position. For example, the platform may include an adhesive, clips, screws, or other mechanical means to secure the substrate. Alternatively, the substrate may be releasably secured using a vacuum applied to at least one surface of the substrate. Preferably, an upper surface of the platform that contacts a lower surface of the substrate is provided with holes. Applying a vacuum to the holes releasably secures the substrate to the platform. Additionally, as discussed below, the platform can be configured to move in one or more dimensions to position the sites at desired analysis positions. The platform can be of integral or unitary construction with any substrate suitable for use with the present invention.

In another embodiment, a surface of the substrate may contain raised or depressed regions on which a sample is located. For example, the sites can be microfabricated depressions or raised features formed on a substrate surface. Thus, the surface may be configured with pits, trenches, v-grooves, mesa structures, or the like. Alternatively, the surface of the substrate can be substantially free of depressions or raised features. In either case, sites supported by the substrate can be functionalized with a probe configured to associate with a desired target to provide measurable fluorescence. Probes and targets are discussed below. Preferably, the sites are formed in a two-dimensional m×n array of discrete sites. By discrete it is meant that the fluorescence from a given site can be measured without the fluorescence from any other site causing substantial interference with the measurement. The surface may also be provided with reflective "mirror" structures for maximization of emission collected therefrom.

Each site preferably contains one or more probes. Probes are any species that can associate with at least one target. Preferably, the probe associates only with one or a few specific targets. The probes are preferably surface-immobilized (bound) at each site. Alternatively, the probes can be immobilized within an interior of the substrate. In any case, preferred arrays of sites comprise at least one of nucleotides, proteins, and peptides. Examples of probes that accommodated at an array of sites include, but are not restricted to agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

Targets are any species that has an affinity for a given probe. Targets may be naturally-occurring or manmade. Also, they can be employed in their unaltered state or as aggregates with other species. Targets include molecules that are attached, covalently or noncovalently, to a binding member that has an affinity for a probe. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended.

In one embodiment, the probes are DNA strands with a specific sequence that is complimentary to a section of a target DNA sequence. Referring to FIG. 1, one end of the DNA probe is chemically (covalently) anchored onto the surface of the solid substrate to provide a chip 300 with an array of probe nucleotides. Thus, the sites can comprise regions of the substrate that include different probes immobilized at a surface of the substrate or to a surface supported by the substrate. When the sites are treated with the sample solution containing target DNA under conditions sufficient to allow hybridization, target DNA with a section of sequence complementary to the probe will anneal to the probe. The amount of target DNA annealed to the probe site is a function of the concentration of the target DNA in the sample solution. Because the target DNA molecules are tagged with a fluorescent dye and the probes are not, the increase of fluorescence signal at each assay site indicates the target DNA concentration in the sample solution. Non limiting examples of fluorophores suitable for use as fluorescent tags with the present invention include Rhodamine dyes, fluorescein dyes, and cyanine dyes.

Different samples may contain the same target DNA. For example, different samples containing different amounts of the same target may be acquired at different times from a cell culture during a drug testing study. If the targets in these samples are tagged with different dyes, the level of the same target DNA in the different samples can be screened on a single assay site by pooling (multiplexing) the samples together and hybridizing on one chip. Because individual sites can be exposed to a single sample that contains contributions from a plurality of samples, site to site variations in response are eliminated. The present invention allows the target DNA level in each of the different samples that contribute to the observed fluorescence to be determined.

Transmission Grating Beam Splitter

The present invention preferably includes a light diffracting element, such as a grating, which can be operated either in reflection mode or in transmission mode. The light diffracting element disperses the fluoresced light from an array of sites allowing a fluorescence spectrum to be obtained. A grating is a diffracting element because light dispersion occurs substantially as a result of diffraction. In contrast, a prism disperses light by refraction, not diffraction. The grating can be planar or curved to act as both a focusing element and a diffracting element. In either case, the diffracting element is preferably operated in transmission mode rather than reflection mode.

Figure 2:
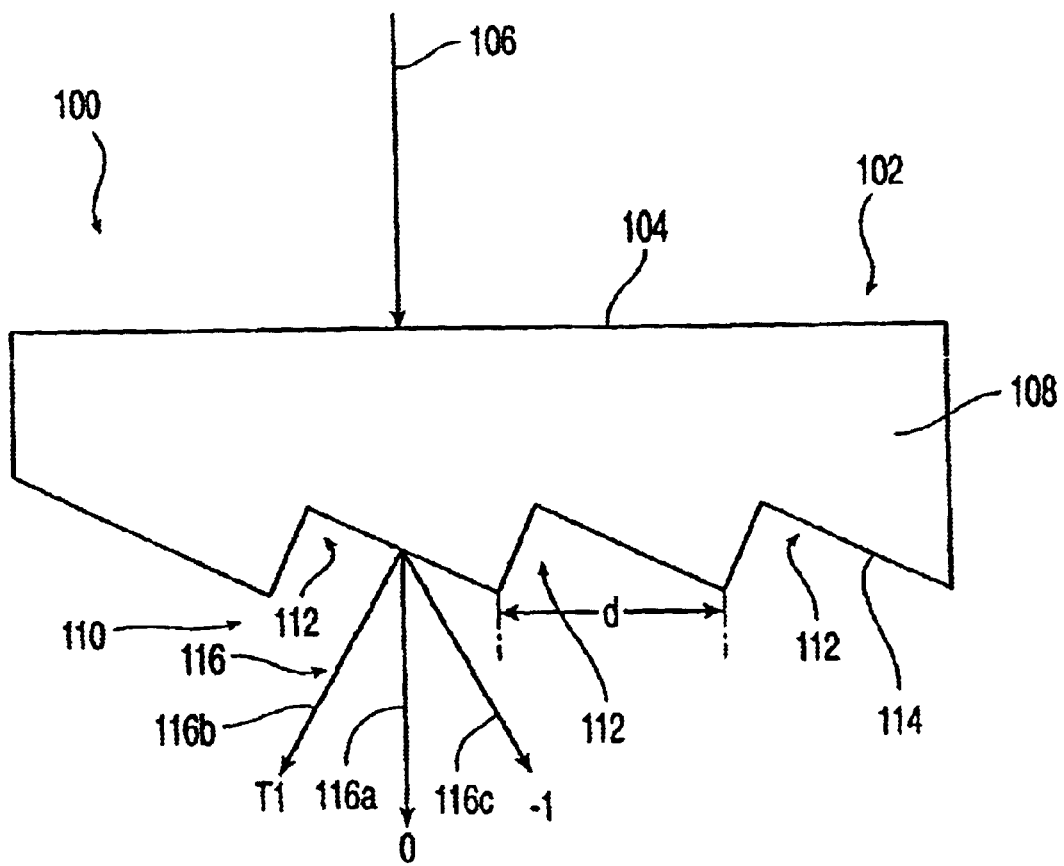
FIG. 2 shows a transmission grating beam splitter, such as that used in the present invention.

FIG. 2 shows a typical transmission grating, a transmission grating beam splitter (TGBS) 100 of the sort suitable for the present invention. The TGBS of FIG. 2 has a first side 102 formed with an incident surface 104 on which incoming light 106 impinges, a substantially transparent body 108 through which the incoming light passes, and a second side 110 from which the split light emerges. As shown in FIG. 2, the second side 110 is provided with a plurality of grooves 112 having a width d, each groove being provided with an angled exit surface 114 forming a wall of that corresponding groove.

The incident light 106 passes through the first surface 104, the body 108, and emerges as a split beam 116 from one of the angled exit surfaces 114. As seen in FIG. 2, the split beam comprises a $0^{th}$ order beam 116a, a +1 order beam 116b and a −1 order beam 116c. The light can also be diffracted into higher order components. These higher order components also provide dispersed light and can be used with the present invention.

As is known to those skilled in the art, a TGBS is typically formed from quartz, glass, plastic, or other suitable, substantially transparent material selected for its index of refraction. The behavior of a TGBS is described in technical note TN 35-51 entitled "Transmission Gratings", published by the Richardson Grating Laboratory Division of the Milton Roy Company of Rochester, N.Y. A preferred TGBS has a size of about 1"×1" although other sizes and shapes can be used. Gratings of this type include gratings available from Edmund Scientific of Barrington, N.J. and from Omega Optical.

A grating can be considered an n-slit system used in Fraunhofer diffraction with interference arising from division of the incident, plane wave front. A planar grating does not focus the light. For a planar grating, the angle of diffraction $\theta$ for light of a wavelength $\lambda$ that is diffracted into an order p is given by:

$$p\lambda = d(\sin \theta + \sin \phi) \tag{1}$$

where d is the distance between the grooves or lines on the grating and $\phi$ is the angle of incidence. Conventionally, light from a slit or other point source is first collimated before it passes through a planar transmission grating. Collimating the light straightens out the light beam to thereby form a plane wave which impinges on the transmission grating with a uniform angle $\phi$. Most often, this angle of incidence is 0° (normal to the transmission grating) because when $\phi=0°$, the above equation reduces to the simplified equation for diffraction through a grating:

$$p\lambda = d \sin \theta$$

However, this simplified equation assumes that a planar wave is incident upon the grating. If the light impinging upon the grating is not collimated, such as being divergent or convergent, the simplified equation does not correctly predict the angle of diffraction for light of a given wavelength. Accordingly, most systems collimate light from a point source before it impinges on a grating.

Applicants have found, however, that an array reader that includes a diffracting element arranged to receive non-collimated fluoresced light provides surprising advantages in light collection efficiency. Arranging the diffracting element to receive non-collimated light increases sensitivity and reduces the detection limits of the apparatus by enhancing the intensity the light that impinges on the detector elements. The present invention also provides a fluorescence detector having sufficient resolution, i.e., a sufficiently small point spread function, to measure fluorescence even from high density arrays. Moreover, the resulting optics have a reduced size and complexity because systems that collimate fluoresced light typically require both a collimating element to collimate the light and a focusing element to focus the collimated light. The present invention, however, does not require a pair of optics to first collimate and then focus the light. By reducing the requirement for multiple light focusing elements, the present invention provides an optical system having greater robustness and resistance to alignment problems.

Fluorescence Detection

Figure 3A:
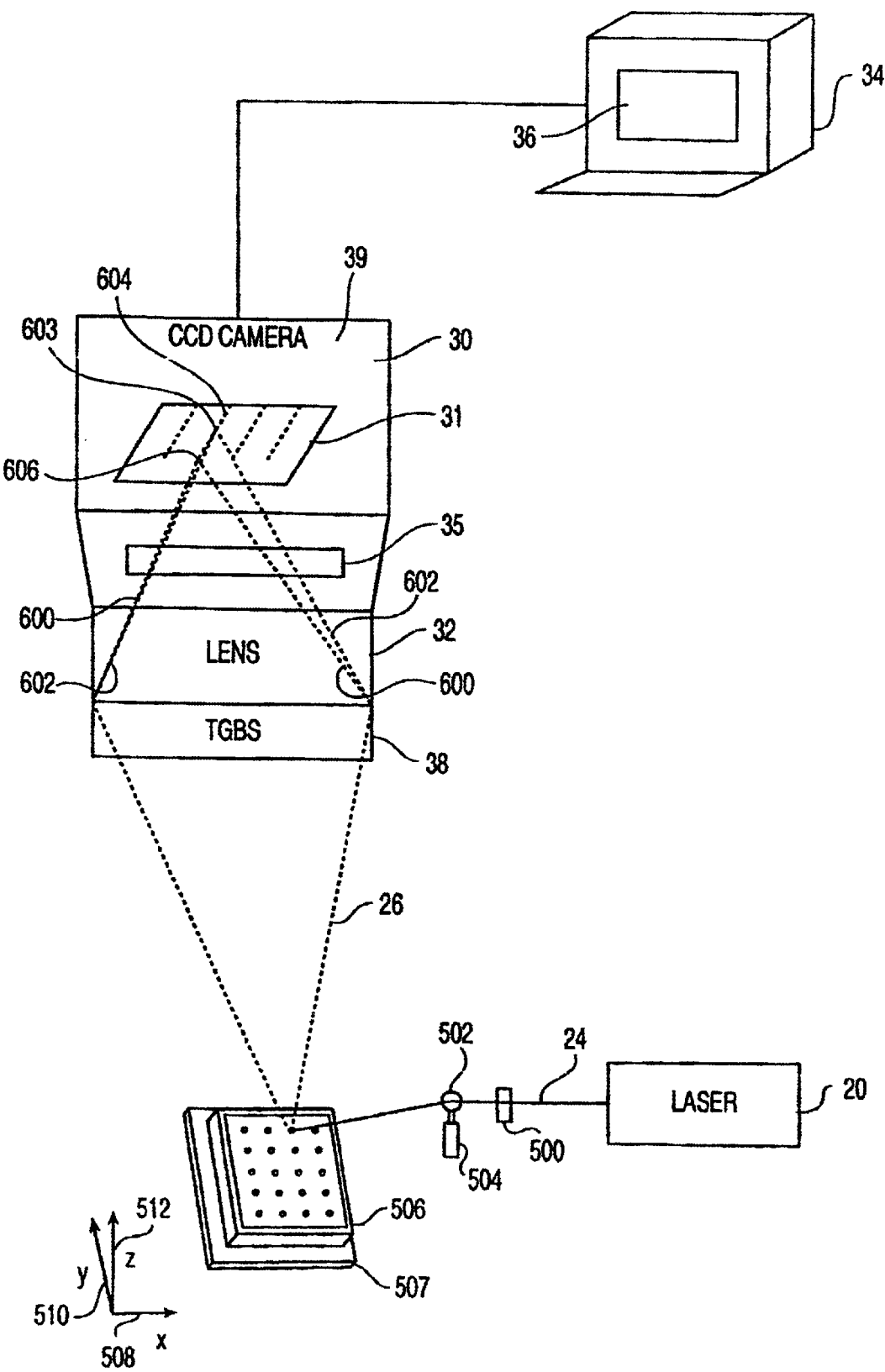
FIGS. 3a & 3b show two embodiments for an array reader in accordance with the present invention.

FIG. 3a shows the environment and preferred arrangement of the present invention. A laser 20 is used to provide excitation light 24 to illuminate a row of sites, which extend parallel to one another. Preferably, the wavelength content of the excitation light is selected to excite fluorescence from each fluorophore present in a site. In the preferred embodiment, the laser 20 is a 100 mW air cooled Argon ion laser. Alternatively, a laser simultaneously lasing at a plurality of discrete wavelengths between, for instance, 460–514 nm may be used to provide excitation light. The present invention, however, is not limited the use of an argon ion laser. A solid state laser lasing at 532 nm is a preferred laser. Any light source that provides excitation light at one or more excitation wavelengths that is suitable for obtaining fluorescence from a desired fluorophore can be used. Suitable, light sources include, for example, krypton lasers, Nd:Yag lasers, diode lasers, titanium sapphire lasers, helium neon lasers, mercury lamps, flashlamps, and the like.

The excitation light 24 in the embodiment of FIG. 3a illuminates a single site at any given instant. Therefore, a beam steering optic such as a mirror 502 can be provided to direct the excitation light to illuminate one or more sites. A galvonometer 504 can be provided to impart computer-controlled motion to the beam steering optic to cause the excitation light to illuminate a plurality of sites in sequence, such as to scan a row or array of sites. Optics 500 can be provided to modify the intensity profile of the excitation light before it impinges upon each site. Preferably, optics 500 comprise at least one lens, such as a plano-convex lens or a best-form laser lens.

As shown in FIG. 3a, the excitation light is directed at an acute angle relative to the plane formed by the row of sites, rather than being directed normal thereto. Preferably, this angle is on the order of 10–30° relative to the plane, and thus 60–80° relative to the normal.

When the fluorophores at a site are illuminated by the laser 20, the fluorophores fluoresce and produce an incoming light 26, represented by broken lines, directed towards a diffracting element such as a transmission grating beam splitter 38 ("TGBS"). The broken lines representing the incoming light 26 also represent an optical path between the substrate and TGBS. As the fluoresced light propagates away from the sites it is non-collimated because it diverges. Thus, unless the fluoresced light is first collimated before reaching TGBS 38, the fluoresced light will remain non-collimated. Typically, a light focusing element such as a lens or mirror is required to collimate the light. In the optical arrangement shown in FIG. 2a, however, the TGBS is arranged to receive divergent non-collimated fluoresced light. The TGBS preferably separates the fluoresced light into a $0^{th}$ order component represented by lines 600 and a higher order dispersed component represented by lines 602. Lines 602 also represent an optical path from the TGBS to the detector.

After being dispersed by the TGBS, the fluoresced light 26 is received by a detector such as a CCD 31. The preferred detector 31 is a scientific grade CCD detector, that is thermoelectrically cooled and back illuminated. The detector 31 has a pixel readout rate at least about 100,000 kHz, preferably at least about 1 MHz. The resolution of detector 31 is preferably at least 16 bit. Detector 31 includes a preferably rectangular array of rows and columns of pixels. Preferred sizes include, for example, arrays of 165 rows and 1100 columns, 100 rows by 1340 columns, and 500 rows by 2048 columns. Detector arrays suitable for use with the present invention include detectors available from Roper Scientific and from SpectraVideo, which sells a #ST001Ev camera, available from PixelVision of Beaverton, Ohio. A light detector suitable for use with any embodiment of the present invention includes an array of light sensitive elements to sense the fluoresced light. Each light sensitive element is configured to measure an intensity of light impinging thereon. Non-limiting examples of light sensitive elements include detectors based on the photoelectric effect, such as photomultiplier tubes, and solid state detectors such as photodiodes. The detector may be a one-dimensional detector, such as a diode array, which comprises a plurality of light sensitive elements disposed along a single dimension, which is generally a straight line. As discussed above, however, the preferred array of light sensitive elements is a two-dimensional array of light sensitive elements such as the pixels of a charge-transfer-device (CCD or CID). When compared to a diode array, a CCD or CID has a plurality of light sensing elements arranged along each of a plurality of different sensing dimensions, such as a row or column of light sensing elements. It should be kept in mind, however, that for the present purposes, a "row" or "column" are equivalent.

Returning to FIG. 3a, the dispersed fluoresced light 602 is preferably detected by a set of light elements 603 arranged along a column 604. The $0^{th}$ order component is preferably received by a first set of light sensitive elements 606, which set is spaced apart from the light sensing elements along dimension 604. As discussed below, a distance between the set of elements 606 and a given member of the set of elements along dimension 604 is indicative of a wavelength of light received by that member. From the detector array 31 within the camera 30, the detected intensities are sent to a processing unit, such as a personal computer 34, or like, having a display 38 and associated memory storage (not shown).

If the array of site to be illuminated is small enough that all of the sites can be arranged to fit simultaneously within the field of view of the detector, all of the sites can be illuminated by using the beam steering device to direct the excitation light sequentially to each site without having to move the sites with respect to the detector. Alternatively, the array of sites to be illuminated may not fit within the field of view of the detector. In this case, the substrate supporting the sites can be moved with respect to the detector to bring new sites within the field of view of the detector. The substrate to be moved is secured, preferably releasably, on a platform 506, which preferably comprises a translation stage 507. Platform 506 and translation stage 507 can be of unitary construction or of integrated construction. Translation stage 507 preferably allows the substrate to be moved in at least one and preferably two dimensions with respect to the detector, such as an x dimension 508 and a y dimension 510. Platform 506 can preferably be positioned with a resolution of at least about 5 $\mu$m and can be moved in steps of less than about 5 $\mu$m.

Using a combination of sequentially scanning the excitation light from site to site and moving the sites with respect to the detector, an entire array of sites can be illuminated. Techniques and apparatus for directing excitation are described in aforementioned U.S. application Ser. No. 09/413,355. For example, to scan an array, the excitation light can be directed, such as scanned, to sequentially illuminate a row or array of sites that are presently within the field of view of the detector. Subsequently, the platform moves the sites with respect to the detector, such as in at least one of the x and y dimensions, to bring different sites within the field of view of the detector. Once the new sites are present within the field of view, the excitation light can be directed to illuminate the newly viewed sites. Preferably, the directing of the excitation light and the site motion are controlled by computer. Translation stage 506 can also be configured to provide motion in a z dimension 512, which is along the optical path taken by fluorescence reaching the TGBS. Moving the sites along the optical path can assist in focusing fluorescence from the sites onto the detector.

Before reaching the detector array 31, the incoming light 26 preferably passes through additional optics such as an optional light focusing element such as a lens 32 and an optional spectral filtering element 35. In the preferred embodiment, the lens is a multi-element lens. For the purposes of this invention, a multi-element lens, such as a camera lens, is considered to be a single light focusing element. Alternatively, the light focusing element may be a single element lens, such as a plano convex lens or a mirror, such as a parabolic mirror illuminated off-axis. The TGBS may be integrated into the camera 30 or lens 32. The TGBS may be of unitary construction with the light focusing element.

A filter 35 is optionally provided to filter the light before impinging on the detector array 31. The purpose of the filter 35 is to allow fluorescent light of interest to pass therethrough, while attenuating light in wavelengths not of fluorescent interest, such as the wavelengths of the excitation light 20. Although the filter is shown positioned between the TGBS and the detector, the filter may be placed at any point between the sites and the detector along the path taken by fluoresced light from the sites to the detector. This is true with respect to any of the optical arrangements discussed herein. Examples of filters which may be used include a Raman notch filter, available from Kaiser Optical Systems of Ann Arbor, Mich., and a longpass filter having a cut-off of 515 nm, available from Spinder & Hoyer Inc., of Milford, Mass. In general, one may use filters which pass wavelengths at which fluorescence of interest is expected, and block wavelengths at which no fluorescence of interest is expected. For instance, one may wish to block the wavelength of the excitation light 24 from the laser 20. As shown in FIG. 3a, the TGBS, the lens and the filter are all attached to the camera 30, thus obviating the need for freestanding optical elements.

Figure 3B:
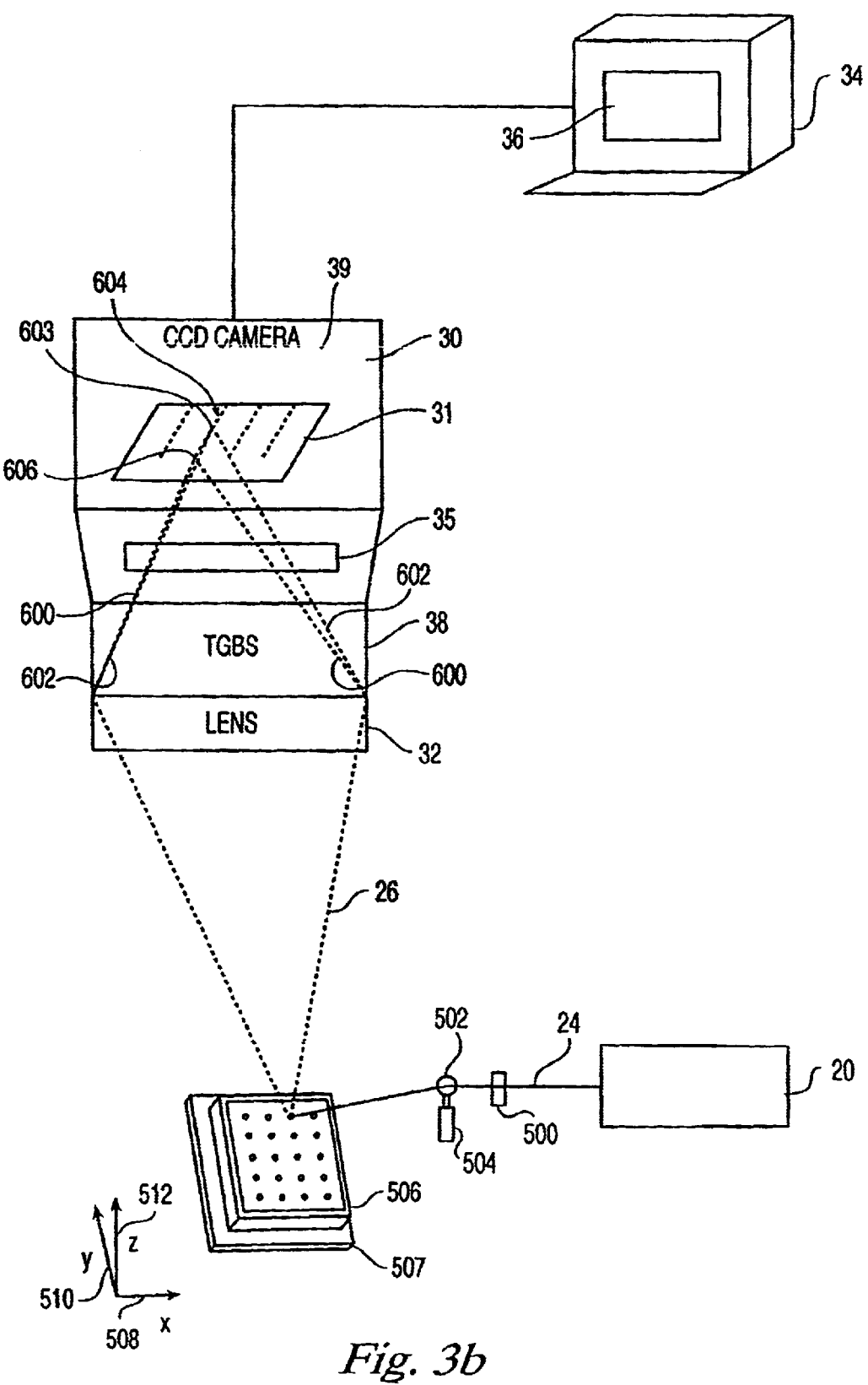

FIG. 3b depicts an alternate embodiment of the array reader in which the TGBS is positioned between the lens 32, and the detector 31. Preferably, the array reader comprises a single light focusing element disposed along an optical path between the substrate and the detector, with the light focusing element being disposed between the substrate and the TGBS. In this alternate embodiment, the spacing between the array of sites and the camera lens is preferably about 3 cm, the spacing between the camera lens and the TGBS about 0.5 cm and the spacing between the TGBS and the detector array 31 is about 4 cm. As is known to those skilled in the art, these spacings depend on the focal length of the lens, and the thicknesses of the optical components. In the embodiment of FIG. 2b, the TGBS is arranged to receive convergent non-collimated light, which has been optically altered by the light focusing element, lens 32.

Figure 4A:
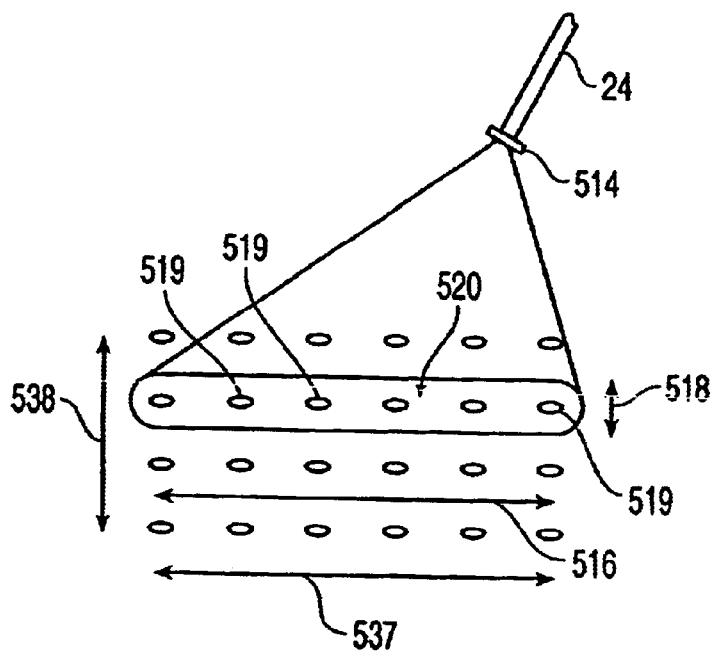
FIGS. 4a and 4b an excitation light configured to illuminate a plurality of sites according to the invention.
Figure 4B:
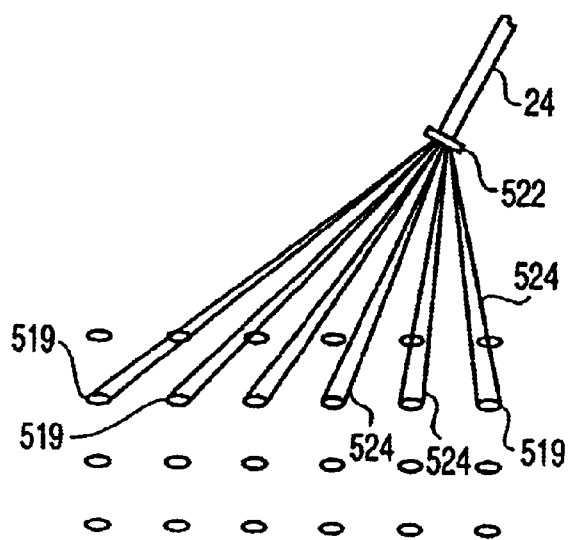

FIGS. 4a and 4b show an embodiment to allow more than one site to be illuminated simultaneously by the excitation light. In this embodiment, a beam expander 514 is used to expand the beam in at least one expanded dimension 516. Preferably, the beam is focused by beam expander 514 in a focused dimension 518, which is usually orthogonal to expanded dimension 516. Techniques and apparatus for expanding a laser beam in one dimension are described in U.S. application Ser. No. 09/413,355, filed Oct. 6, 1999, which incorporated above. Beam expander 514 may comprise a telescope including a negative cylindrical lens to expand the excitation light in the expanded dimension 516 and a negative cylindrical lens to focus the excitation light in the focused dimension 518. Commercial line generators are also available to modify light beams in this way. After the excitation light passes through the beam expander, it appears as a thin line 520, which can illuminate a plurality of sites 519 at a given instant.

As an alternative to a beam expander, one or more beam splitters 522 may be used to separate the excitation light into a plurality of excitation beams 524. Each excitation beam 524 can be directed to illuminate a single site at any given moment. The combination of excitation beams 524, therefore, illuminates a plurality of sites simultaneously.

Excitation line 520 or plurality of excitation beams 524 can substantially replace the need to sequentially direct the excitation light to different sites. For example, as shown in FIG. 4a, excitation line 520 is arranged to illuminate all of the sites along a dimension 537 of the array of sites. Therefore, all of the sites in the array of sites can be illuminated by moving the sites along a dimension 538 to illuminate successive rows of sites extending perpendicular to dimension 538. As new sites are moved into the field of view of the detector and illuminated by the excitation line, fluorescence from the illuminated sites is dispersed by the TGBS and received by the detector 31.

Figure 5:
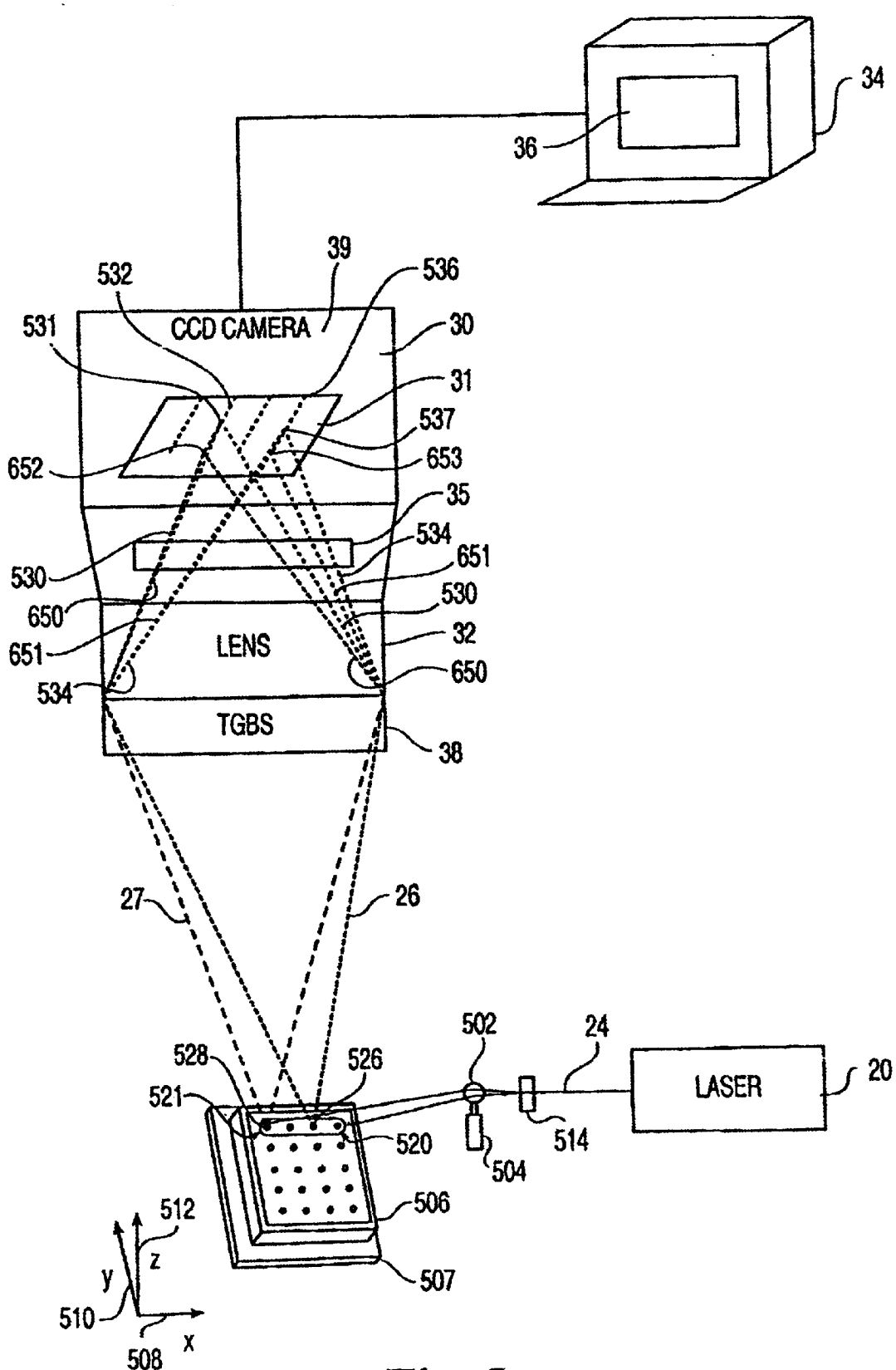
FIG. 5 shows another embodiment of an array reader in accordance with the present invention.

FIG. 5 shows excitation line 520 used to illuminate a plurality of sites along a row 521. For clarity, FIG. 5 shows fluoresced light 26 and 27 originating from only from first and second sites 526 and 528 respectively. It should be understood, however, that excitation line 520 illuminates all of the sites along row 521 and that fluorescence will result from fluorophores present in the sites. Fluoresced light 26 and 27 is dispersed by the TGBS onto different portions of the detector to allow a fluorescence spectrum of each illuminated site to be obtained. For example, fluoresced light 26 from site 526 is dispersed by the TGBS to provide dispersed fluorescence 530, which impinges upon a plurality of light sensitive elements 531 arranged along a column 532. Fluoresced light 27 from site 528 is dispersed by the TGBS to provide dispersed fluorescence 534, which impinges upon an plurality of light sensitive elements 537 arranged along a second, different column 536. The TGBS preferably separates fluoresced light 26 and 27 into different $0^{th}$ order components represented by lines 650 and 651, respectively. The $0^{th}$ order components 650 and 651 are preferably each received by at least one respective light sensitive element 652 and 653 of detector 31.

Figure 6:
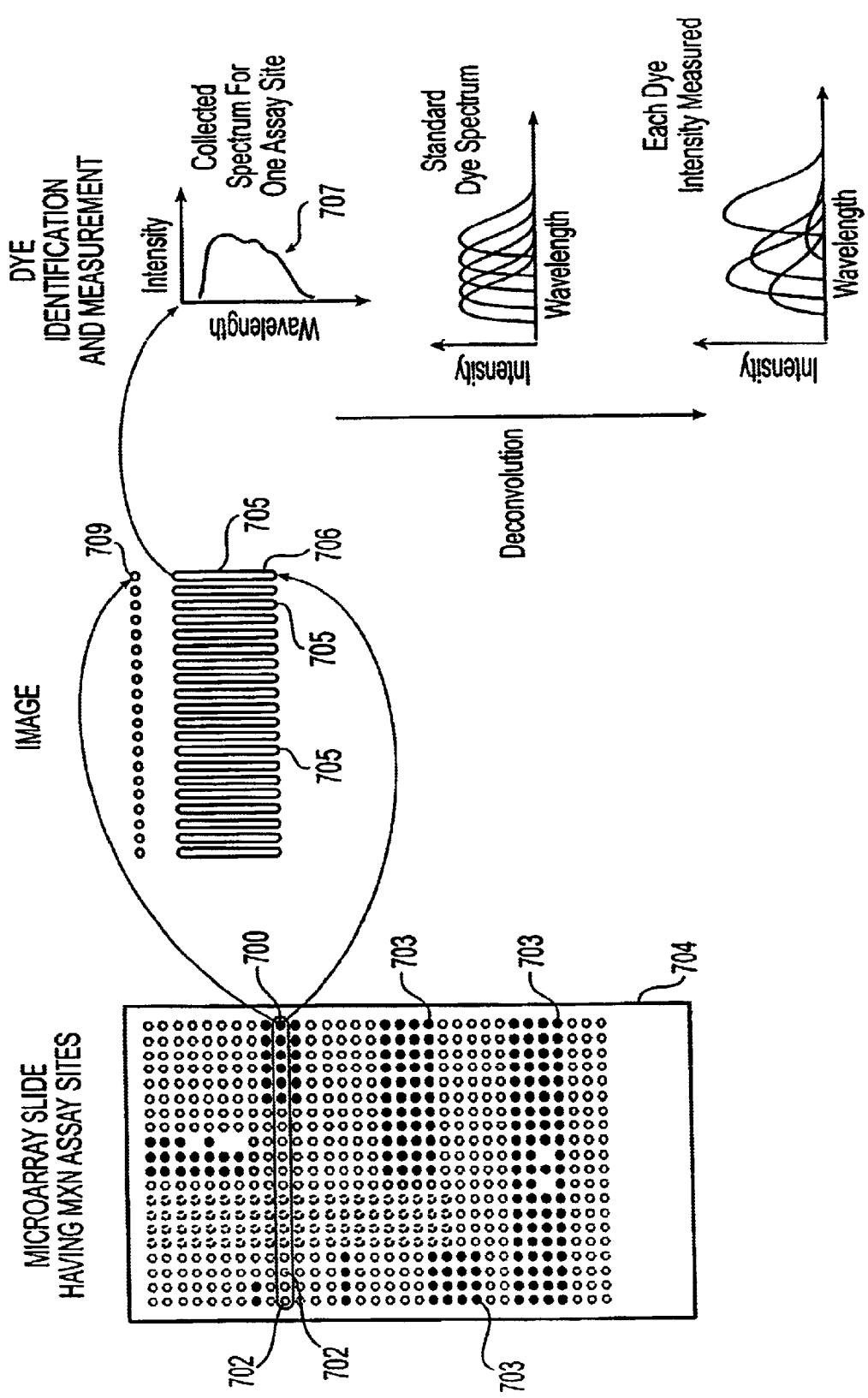
FIG. 6 shows the deconvolution of fluorescence intensities measured using the array reader of FIGS. 3a, 3b, or 5.

FIG. 6 schematically illustrates the effect of using an array reader of the present invention to detect fluorescence from a row 700 of illuminated sites 702 supported by a substrate 704. Fluorescence does not arise from non-illuminated sites 703. Light sensitive elements (not shown) arranged along different columns 705 of the detector receive dispersed fluorescence 706 from different illuminated sites 702. The detector also receives $0^{th}$ order light 709 from each site. From the detector, the detected intensities are sent to a processing unit (not shown) that provides intensity-wavelength data 707 for the fluorescence detected along each column 705. For clarity, FIG. 6 shows intensity-wavelength data resulting from only one of the illuminated sites.

Figure 7:
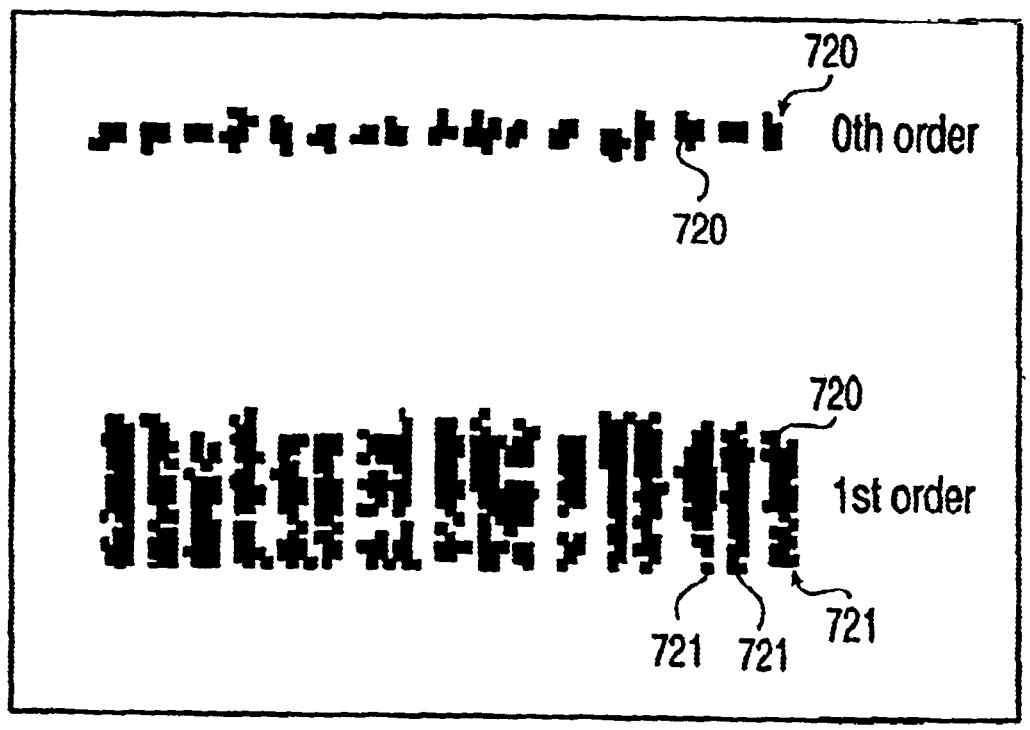
FIG. 7 shows the array reader output with a reader having a transmission grating beam splitter.

FIG. 7 is a sample display from a CCD detector output that illustrates the pattern of light intensities that can be observed by light sensitive elements of the detector. Each dark square 720 represents a light sensitive element that has detected a measurable intensity of light. As can be seen in these figures, non-dispersed $0^{th}$ order light components extend over only a limited number of light sensitive elements 720. On the other hand, the members of the 1st order band extend along respective column 721 illustrating the wavelength dispersion of the higher order components. The availability of both the $0^{th}$ order non-dispersed components and the higher order components allows for enhanced flexibility in subsequent data analysis.

Figure 8A:
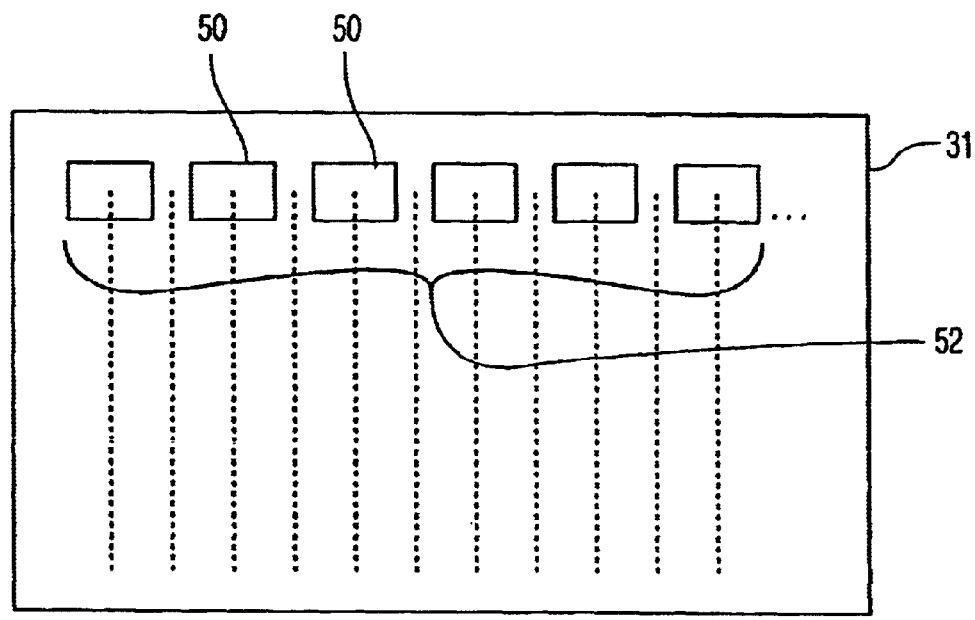
FIG. 8a shows detector array output with a detector not having a transmission grating beam splitter.

FIG. 8a illustrates the effect of using a detector system of the present invention, but with the diffracting element omitted. In the absence of the diffracting element, each illuminated site creates a single fluorescence spot 50 on the detector array 31, and all the illuminated spots together form a row 52 of discrete florescence spots. Nothing else appears on the detector array 31.

Figure 8B:
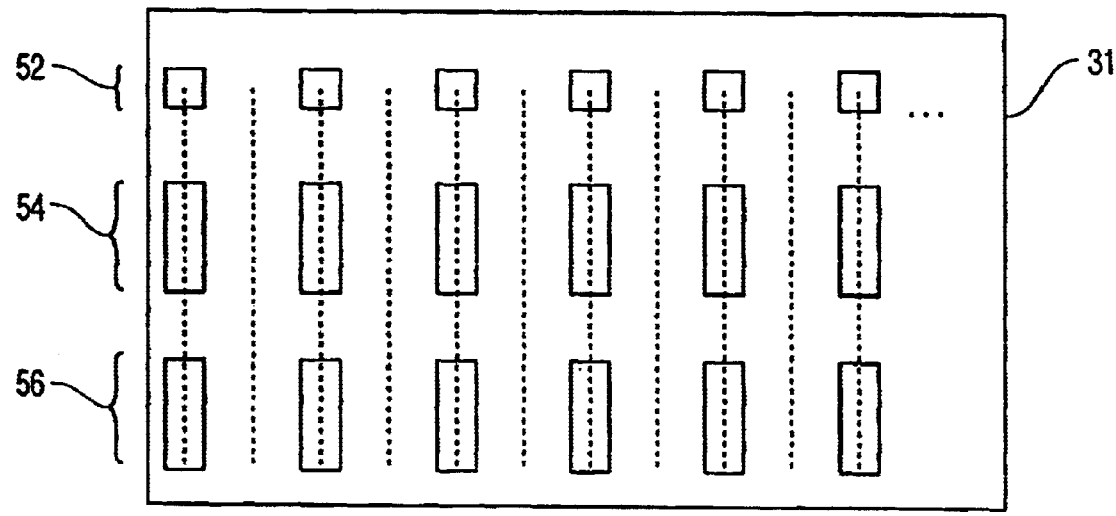
FIG. 8b shows detector array output with a detector having a transmission grating beam splitter.

FIG. 8a illustrates the effect of using a detector system of the present invention with the diffracting element included. When the TGBS is inserted into the system, the florescence from the each site is split into a plurality of bands, each band representing a particular order. Thus, FIG. 8b depicts the formation of a $0^{th}$ order band 52, a 1st order band 54 and a 2nd order band 56. When imaged onto a detector array, each of these bands occupies a plurality of rows of pixels in the vertical direction, with different sites being imaged onto different columns, at least one column of pixels for each site. The $0^{th}$ order band collects the fluorescence from all wavelengths and the members in this band are tightly focused, extending over only one or two rows of pixels for each column corresponding to a site. This occurs because the $0^{th}$ order band is substantially non-dispersed. By contrast, the members in the 1st and 2nd order bands are dispersed, and extend over several rows pixels, along the column(s) corresponding to each site.

To facilitate subsequent processing of the light collected by the detector array, it is preferable that the $0^{th}$ order bands from the sites are imaged onto the same row(s) of pixels, and that their corresponding 1st order bands are imaged onto substantially the same column(s). This alignment obviates the need to later correct for any skew among the received pixels in the sensed image, during subsequent processing. To ensure this, however, one typically may need to rotate the camera, and thus the detector array therein, relative to the illuminated sites.

It should be noted here that diffracting elements such as a TGBS can be selected to favor one or more orders over other orders. In other words, the transmittance in the favored orders can significantly exceed the transmittance in the disfavored orders. Thus, one may produce a TGBS which passes primarily $0^{th}$ and 1st order components, while −1st order and other orders are considerably attenuated.

In the preferred embodiment, the transmission grating beam splitter has 70 grooves/mm. The angular difference between the $0^{th}$ and 1st order is about 2°, and the dispersion angle within the 1st order for wavelengths between 500 nm and 700 nm is only about 0.8°. Thus, the $0^{th}$ and 1st orders from a single site can easily be separated from one another on a detector array having a pixel width of about 25 µm, by judiciously spacing the TGBS from the plane of the array.

Figure 9A:
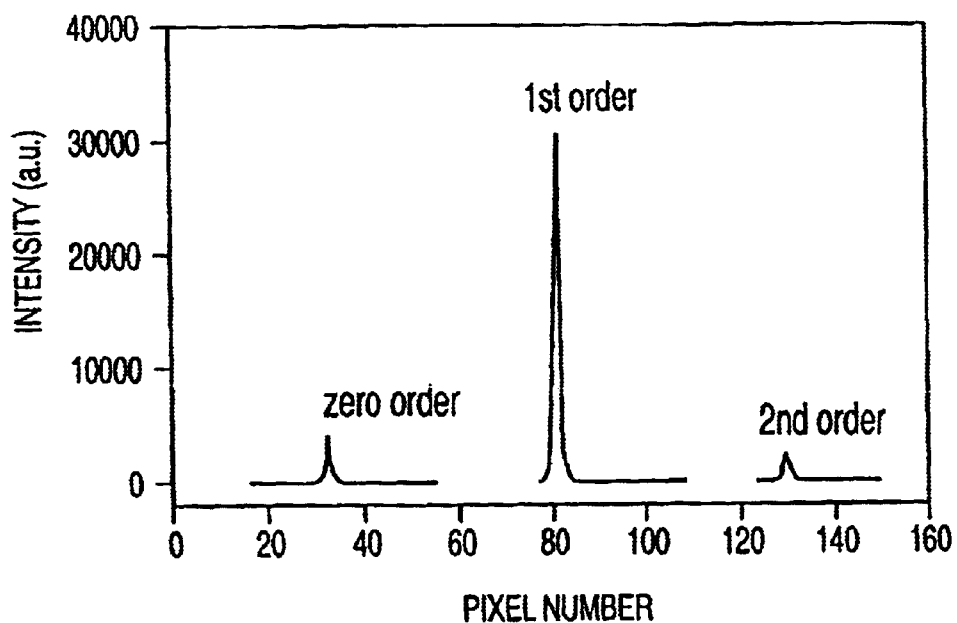
FIGS. 9a and 9b show the response of a detector of the present invention in response to monochromatic illumination of a single site.

FIG. 9a shows the relative separation between, and the spread of, the 0th, 1st and 2nd order components resulting from the excitation light impinging on a single site having no fluorophores present. The resultant light impinges on a lens/TGBS/detector array arrangement that does not have a filter to completely block the excitation light. The excitation light, which is substantially monochromatic, is focused to a small spot occupying an area of 2×2 pixels on the detector array. Thus, this image represents the detector's system response or the point spread function of the detection optics. The intensity distribution of 0th, 1st and 2nd orders is about 1, 7 and 0.6, respectively.

Figure 9B:
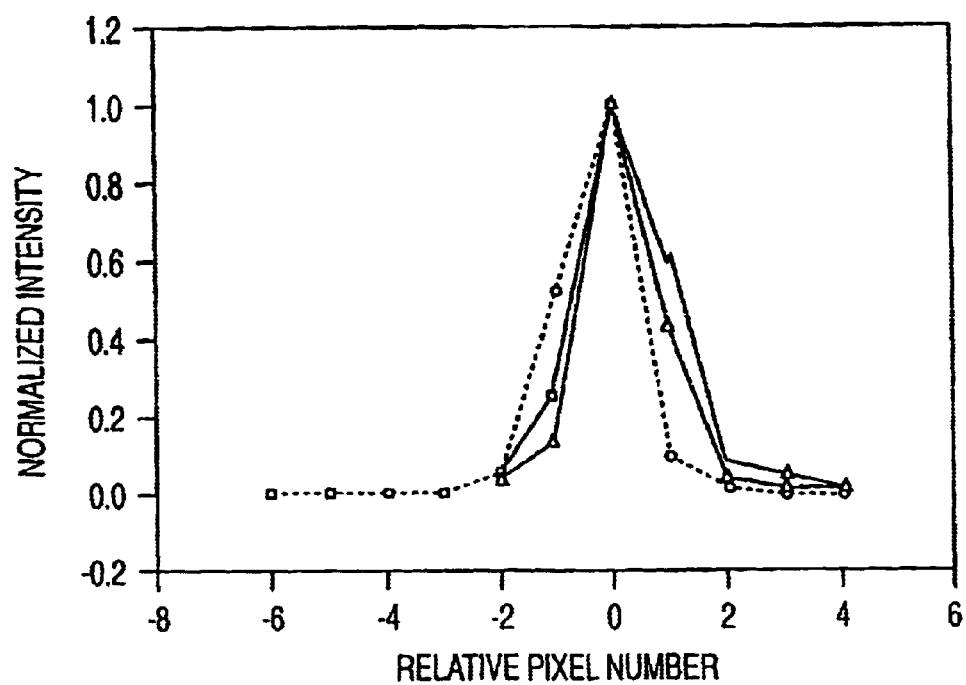

FIG. 9b shows an expanded view of the peaks corresponding to 0th, 1st and 2nd order in FIG. 9a, after normalizing each to an intensity of 1.0, and co-locating them. This figure shows that the spread for each of the peaks in response to monochromatic light is substantially same for each order. In particular, the widths of each peak at half normalized maximum intensity are substantially similar, given the 1-pixel detector resolution. Thus, the image dispersion of the present detector is negligible for 0th, 1st and 2nd orders using monochromatic light.

Figure 10:
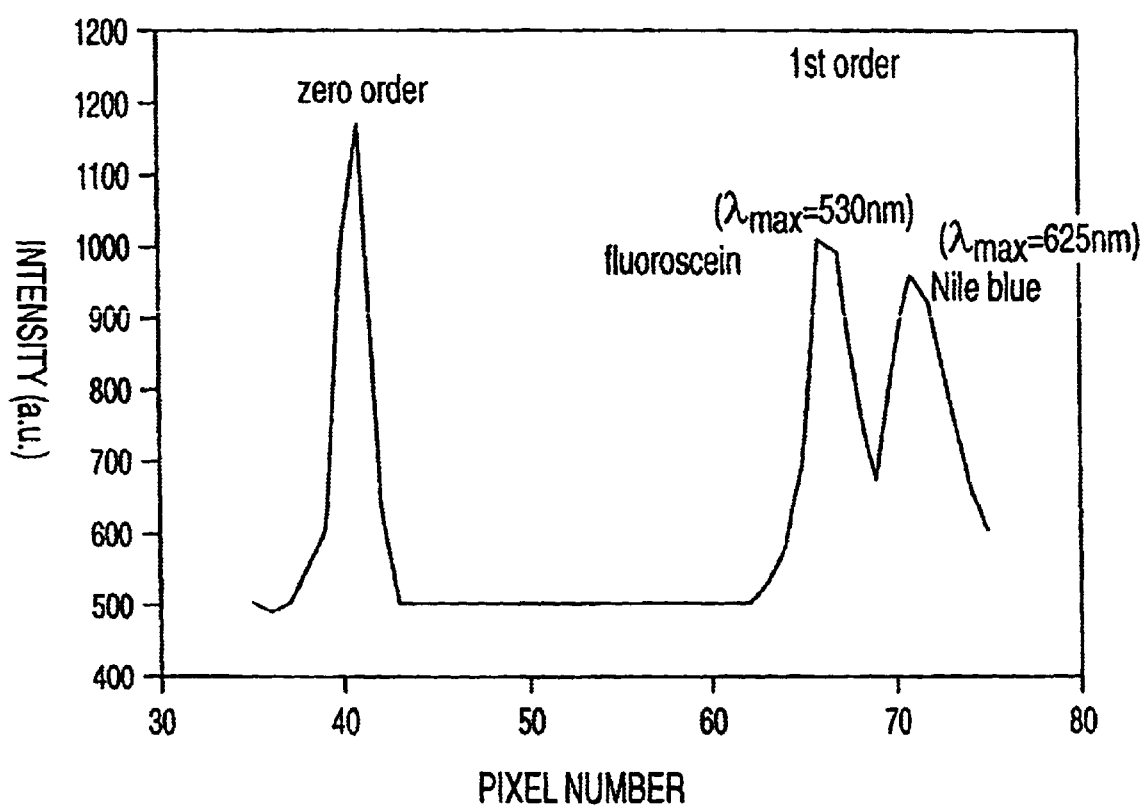
FIG. 10 shows the response of an array reader of the present invention with a site containing two dyes.

FIG. 10 shows the output resulting from illuminating a site occupied by two dyes, fluorescein ($\Lambda_{max}$=530 nm) and nile blue ($\Lambda_{max}$=625 nm), and using the detector of the present system to detect the fluoresced light. Both the 0th order and the 1st order peaks appear, and distinct 1st order peaks appear for each of the two dyes. The $0^{th}$ order confines the non-dispersed wavelengths of fluorescence within one or two pixels in the detector array. In contrast, the 1st order fluorescence components are dispersed across multiple pixels.

Figure 11A:
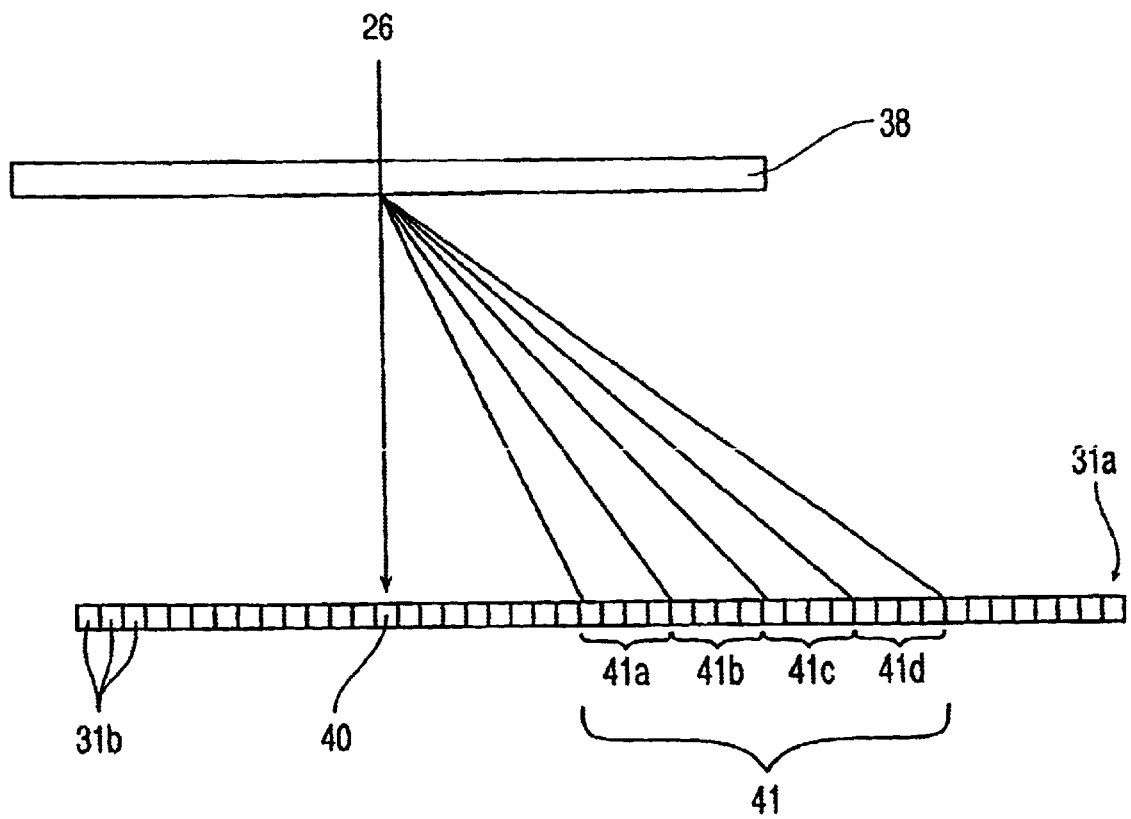
FIGS. 11a and 11b shows a transmission grating beam splitter separating incoming light comprising four wavelength bands.
Figure 11B:
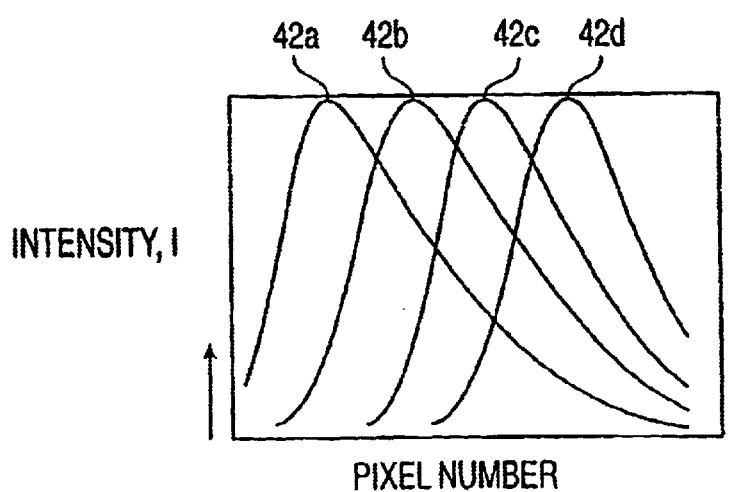

FIGS. 11a and 11b show an example to illustrate the effect of a detector in accordance with the present invention on incoming light 26 from a sample comprising four fluorophores. In this example, the four samples may correspond to the expression of a gene monitored at four different times, as discussed above. The target in each sample comprises the same nucleotide. The nucleotides in each sample have been tagged with dyes that produce different fluorescence spectra 42a, 52b, 42c, and 42d. For simplicity, only the TGBS 38 and one pixel column 31a of the detector array 31, comprising a plurality of pixels 31b, is shown in FIG. 11a. It is understood, however, that the light focusing element can be interposed between the TGBS and the pixel column 31a, or, as described above, the incoming light 26 may have already passed through the light focusing element at this point.

The incoming light 26 is separated into a 0th order component 40 and a 1st order component 41. As shown in FIG. 11a, the 0th and 1st order components are spatially separated from each other, as they impinge on the pixel column 31a. This separation will subsequently allow one to use the intensities of both the $0^{th}$ order and the 1st order transmitted incoming light components when performing subsequent analyses for identifying particular fluorophores, and hence, the amount of target in each of the four multiplexed samples.

As discussed above, each sample of gene's expression pattern is typically tagged with a different fluorophore. To reduce experimental variation, samples are preferably pooled in the same site. In general, if N samples are to be pooled together in a particular site, the number of fluorophores in the site would range from zero to N depending on how many of the samples contain a target having an affinity for a probe disposed at that site. Typically, the fluorophores fluoresce at wavelengths that overlap one another. Therefore, the multiplexed sample approach requires a detection system able to distinguish simultaneously the response from as many as N different fluorophores to maximize the sample analysis rate (throughput). Thus, in FIG. 11a, the detected 1st order light 41 comprises four sub-bands, designated 41a, 41b, 41c and 41d, each corresponding to a region along the column of pixels 31a, in which a particular one of the four fluorophores dominates.

FIG. 11b shows the relative intensity of fluorescence of the four fluorophores as a function of relative pixel number. Here, increasing pixel number corresponds to increasing wavelength. In FIG. 11b, curves 42a, 42b, 42c and 42d correspond to the fluorescence emission spectra of the four fluorophores, each of which is shown to be dominant in a corresponding one of the four pixel regions 41a, 41b, 41c and 41d of FIG. 7a.

As stated above, in FIG. 11a, the pixel column 31a corresponds to the detector output for a single site. And for that one site, data is available for a number of contiguous pixels, including a small number of pixels which have $0^{th}$ order information, and a larger number of pixels which have 1st order information. This offers some flexibility in performing subsequent analysis to determine exactly which fluorophore is present at any given time.

Figure 12:
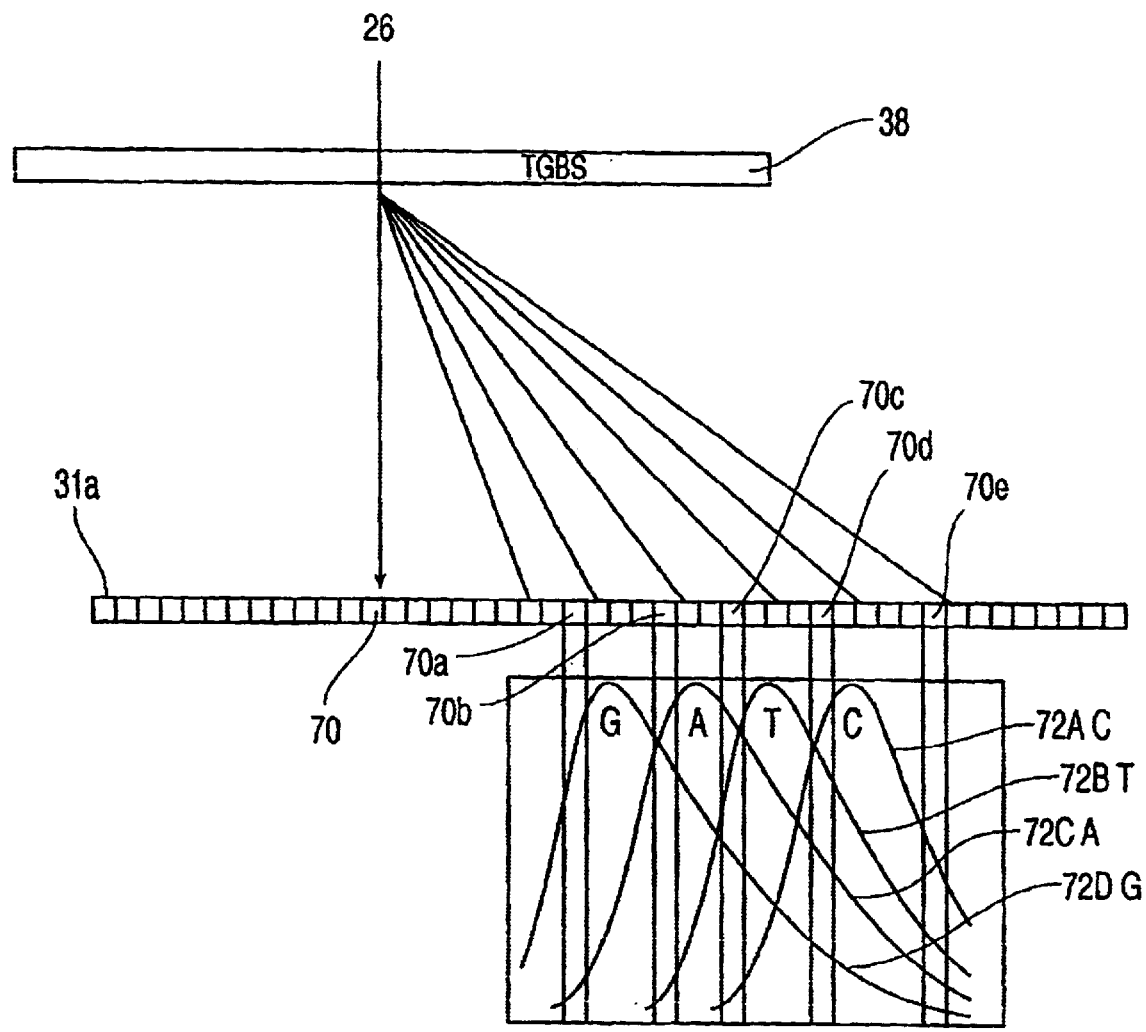
FIG. 12 presents a pixel sampling scheme for identifying fluorescent tags with a detector of the present invention.

FIG. 12 shows how the pixels of the pixel column 31a may be sampled to come up with a detection scheme which exploits the detector of the present invention. In this example, six pixels are monitored. Pixel 70 corresponds to the $0^{th}$ order component, and pixels 70a, 70b, 70c, 70d and 70e correspond to various portions of the first order component. In this example, four fluorophores, which are designated, G, A, T, and C, whose spectral curves are given by 72a, 72b, 72c and 72d, respectively, correspond to the fluorescent tags used in the four gene expression samples discussed above.

Pixel 70a is positioned slightly to the left of the peak for fluorophore G. Thus, it receives much energy contribution from G, and virtually none from the A, T and C. Thus, energy in pixel 70a indicates the presence of G.

Pixel 70b is positioned roughly at the intensity cross-over point between fluorophores which correspond to nucleotides G and A. Thus, signal energy from pixel 70b gets substantially equal contribution from these two fluorophores, and very little from T and C. Thus, energy in pixel 70b indicates the presence of either G or A.

Pixel 70c is positioned near the intensity cross-over point for fluorophores A and T. Pixels 70c receives somewhat less contribution from G, and virtually no contribution from C. Thus, energy in pixel 70c is indicative of A or T, and, to a lesser extent, of G.

Pixel 70d is positioned near the intensity cross-over point for fluorophores T and C. This pixel receives nearly equal contribution from these two fluorophores, somewhat less from A, and considerably less from G. Thus, energy in pixel 70d is indicative of T or C, of A to a slightly lesser extent, and of G to an even lesser extent.

Pixel 70e is positioned to the right of the intensity peak for fluorophore C. At this point, there is relatively little contribution from T, even less from A, and still less from G. Thus, strong energy presence in pixel 70e is indicative of C.

Figure 13:
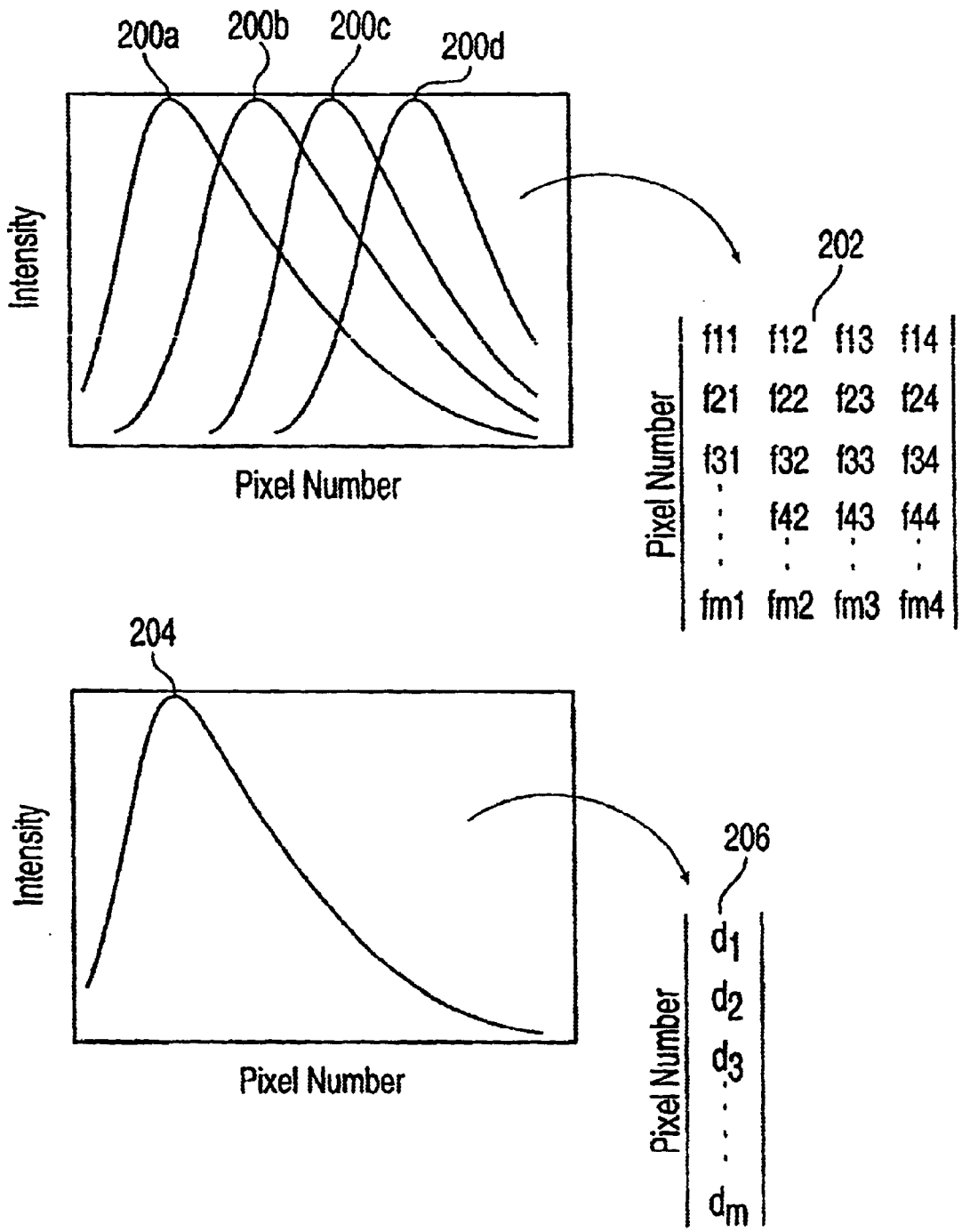
FIG. 13 presents the deconvolution of synthetic spectral data from the pixel sampling scheme of FIG. 12.

Another detection scheme for analyzing the detected fluoresced light is illustrated in FIG. 13. In this example, spectral curves 200a, 200b, 200c, and 200d represent the pixel response (spectral curve) of each of four component dyes in a sample. The spectral curve for each dye represents the response that would be observed by the present array reader for a site containing only that dye. The spectral curves of the dyes can be represented as a matrix 202 having elements $f_{ij}$. Wavelength or pixel number i varies down the M rows of matrix 202 while component number j varies across the N columns. Here, M represents the number of light sensitive elements along the column used to obtain the spectral curves. In this example, N=4 because there are 4 component dyes. The present invention however may be used to resolve at least up to N=M fluorophores.

When fluorescence is received from a site containing some of each of the N dyes, an observed spectrum 204 results. Spectrum 204 contains contributions from each of the N dyes. Observed spectrum 204 can be represented as a vector 206 with elements di. The ith element of vector 206 corresponds to the intensity received by the ith light sensing element along the column. The M elements of vector 206 are given by the sum of the spectral curves of the N component spectra, each weighted by the respective abundance of the dye:

$$d_i = \sum_{j=1}^{N} = f_{ij} c_j$$

Where the jth element of a vector cj contains the abundance or relative amount of the jth dye in the site. The above equation can be written in matrix form as:

$D = FC$

Multidimensional techniques such as least squares regression can be used to estimate the elements of C:

$C = F^{-1} D$ where $F^{-1}$ is the inverse or pseudo-inverse of F. In general, techniques suitable for determining the contributions of each fluorophore to a spectrum observed for a particular site are described in aforementioned U.S. application Ser. No. 09/676,526.

It should be noted that the methodology of the present invention is independent of the particular set of fluorophores being used. Given a new set of fluorophores, one can derive their spatio-spectral characteristics using known techniques with a predetermined excitation wavelength, and then designate appropriate pixels for a detection scheme. It should also be noted that the present detection scheme provides one with more measured values than unknowns because, in general, there will be many more light sensitive elements receiving dispersed light than the number of fluorophores in each site. This contrasts with known ratio-based methods which require solution of underdetermined systems.

Figure 14:
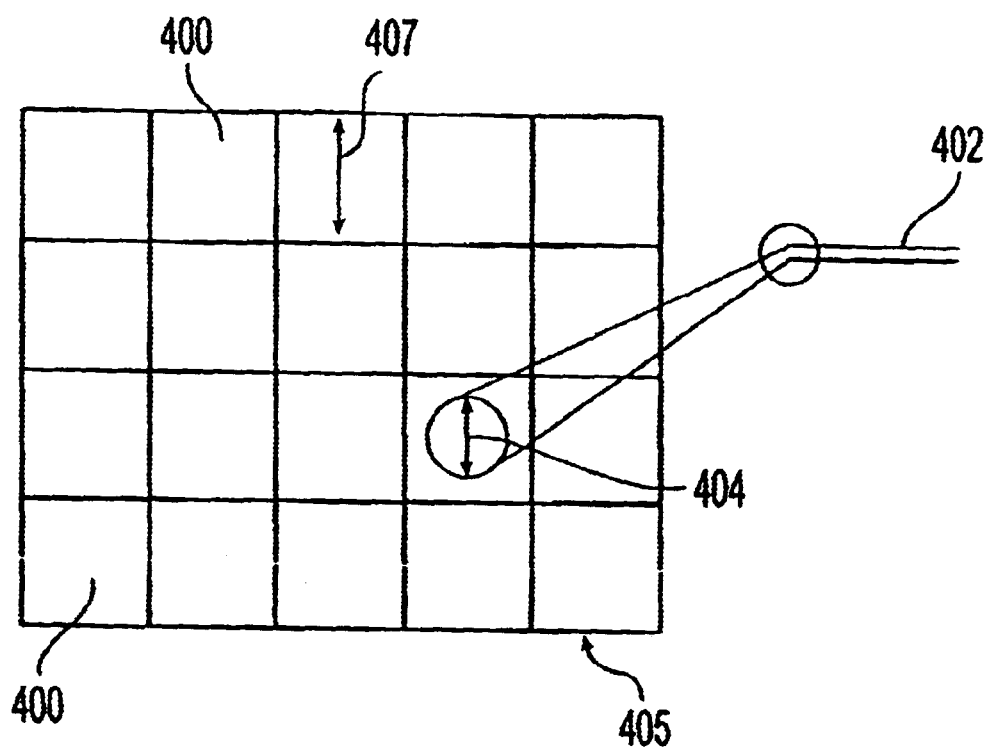
FIG. 14 shows adjacent sites sampled with a focused laser beam according to the invention.

Adjacent discrete sites, need not be separated by a physical barrier but can adjoin one another in one or more dimensions to form a continuous array of discrete sites. For example, as shown in FIG. 14, a series of sites 400 adjoin one another to form a continuous two-dimensional array 405 of different sites. Several options are available to separately interrogate the probes located at each of the different adjoining sites (spots). First, a laser beam 402 can be focused to a have a diameter 404 smaller than the smallest dimension 407 of each site. Second, the fluoresced light can be collected, focused, and detected using optics that have sufficient resolution to allow fluorescence arising simultaneously from two or more adjoining sites to be resolved. Techniques and apparatus for focusing laser beams are described in U.S. application Ser. No. 09/413,355, filed Oct. 6, 1999, which was incorporated above. The present invention is adapted to both approaches for measuring the fluorescence from the sites.

Figure 15:
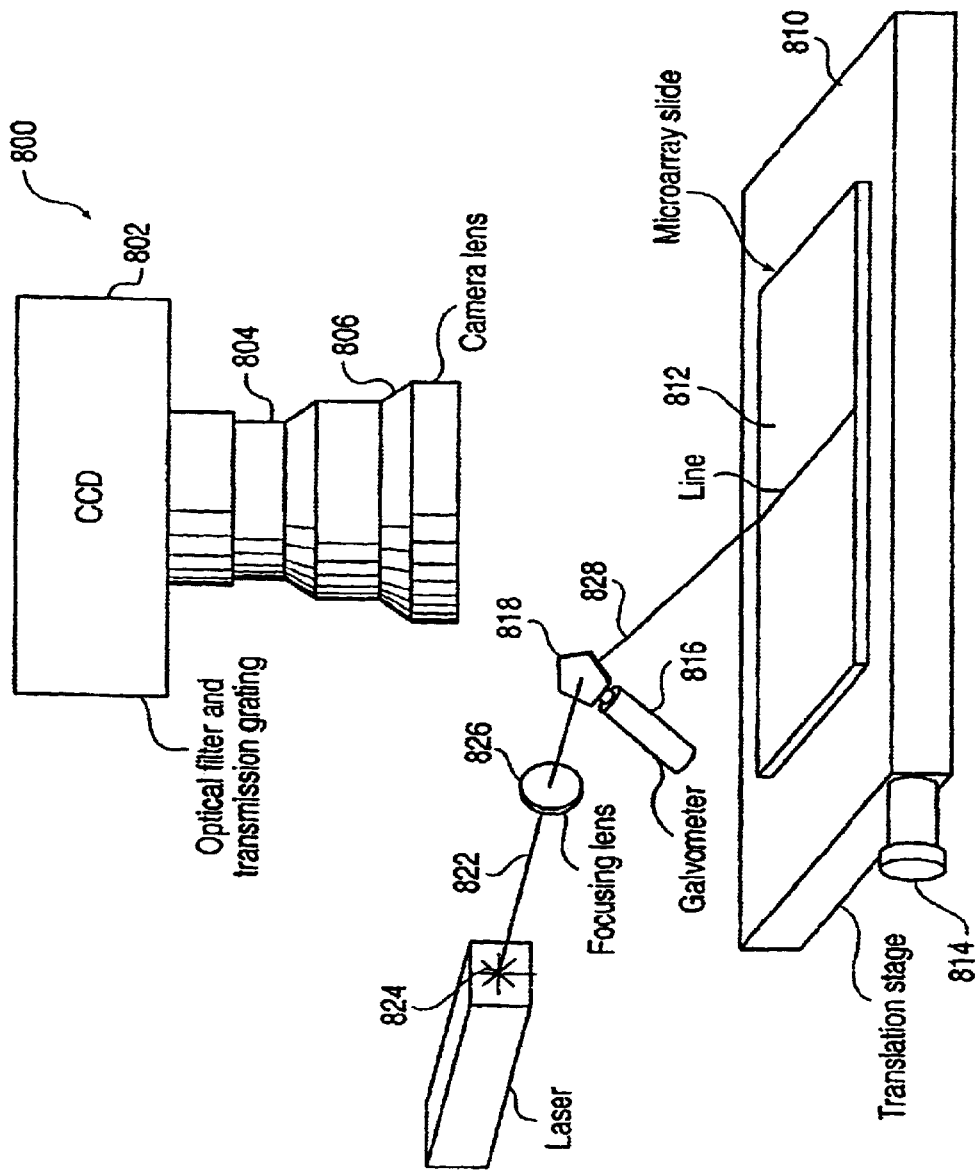
FIG. 15 presents a schematic of another embodiment of an array reader according to the invention.

FIG. 15 presents an embodiment of an array reader in which the camera unit 800 comprises CCD 802, diffracting element 804, and lens 806 which together form an integrated unit. In FIG. 15, the camera unit 800 is seen to be directed towards a platform 810 which supports a substrate 812, seen here as a microarray slide having a plurality of sites(not shown), and a first changing device 814 which moves the platform, and therefore the substrate, relative to the camera unit 800. FIG. 15 also shows a second changing device 816 comprising a mirror 818 and a galvanometer 820 to selectively illuminate a subset of sites on the substrate 812, by altering a direction of light 822 which emerges from the light source 824 and first passes through a focusing lens 826. In the illustrated embodiment of FIG. 15, an entire row of sites on the microarray slide 812 is sequentially illuminated, or scanned. In such an arrangement, the first changing device 814 moves the platform at the conclusion of each row scan to bring a different row of sites to be illuminated during the next row scan.

While the above invention has been described with reference to certain preferred embodiments, it should be kept in mind that the scope of the present invention is not limited to these. For instance, a compound lens may be used, and the filter may be placed between the lens and the TGBS, or even before both of them. Also, a plurality of rows of sites may be imaged simultaneously upon the detector. Thus, one skilled in the art may find variations of these preferred embodiments which, nevertheless, fall within the spirit of the present invention, whose scope is defined by the claims set forth below.

What is claimed is:

1. An array reader comprising:
   a light source configured to emit an excitation light;
   a substrate having a plurality of discrete sites arranged in at least two dimensions, each site configured to support a sample;
   a detector comprising an array of light sensitive elements; and
   a diffracting element disposed along an optical path between the substrate and the detector, wherein
   the diffracting element is configured to receive non-collimated light emitted by at least one sample illuminated by said excitation light.

2. The array reader according to claim 1, wherein the substrate comprises a microtitre tray having a plurality of wells, each well configured to accommodate a sample.

3. The array reader according to claim 1, wherein the substrate comprises a platform.

4. The array reader according to claim 1, wherein the substrate comprises an array of nucleotides.

5. The array reader according to claim 1, wherein the diffracting element is a transmission grating beam splitter (TGBS).

6. The array reader of claim 5, wherein the TGBS separates the non-collimated light received from the at least one sample into a $0^{th}$-order component which is received by a first set of said light sensitive elements and a higher-order component which is received by a second set of said light sensitive elements, the second set being spaced apart from the first set.

7. The array reader of claim 6, wherein each member of the second set is disposed at a distance from the first set which is indicative of a wavelength of light received by that member.

8. The array reader according to claim 5, wherein the non-collimated light is received by the TGBS without first having been optically altered by a light focusing element.

9. The apparatus according claim 8, further comprising a single light focusing element disposed along an optical path segment between the TGBS and the detector.

10. The apparatus according claim 5, further comprising a single light focusing element disposed along the optical path between the substrate and the detector, said light focusing element being disposed between the substrate and the TGBS.

11. The array reader according to claim 1, wherein the substrate comprises a two-dimensional array of sites arranged as a plurality of rows and a plurality of columns.

12. The array reader according to claim 11, further comprising a changing device configured to determine which of said plurality of sites is illuminated at any given instant.

13. The array reader according to claim 12, wherein the changing device alters a position of the sites with respect to the detector.

14. The array reader according to claim 12, wherein the changing device alters a direction of the excitation light so as to selectively illuminate a subset of said plurality of sites.

15. The array reader according to either claim 13 or claim 14, wherein the excitation light is configured to illuminate only one site at a time.

16. The array reader according to either claim 13 or claim 14, wherein the excitation light is configured to illuminate an entire row or an entire column at any given instant.

17. An array reader comprising:
    a light source configured to emit an excitation light;
    a substrate comprising a plurality of sites spatially configured as a two-dimensional array having a plurality of rows and a plurality of columns, each site configured to support a sample;
    a changing device configured to determine which of said plurality of sites is illuminated at any given instant;
    a detector comprising a two-dimensional array of light sensitive elements;
    a transmission grating beam splitter (TGBS) disposed along an optical path between the substrate and the detector; and
    a single light focusing element disposed along an optical path between the substrate and the detector, wherein
    the TGBS is configured to receive non-collimated light emitted by at least one sample illuminated by said excitation light, the non-collimated light being received by the TGBS without first having been optically altered by a light focusing element.

18. The array reader according to claim 17, wherein the changing device alters a position of the sites with respect to the detector.

19. The array reader according to claim 17, wherein the changing device alters a direction of the excitation light so as to selectively illuminate a subset of said plurality of sites.

20. The array reader according to either claim 18 or claim 19, wherein the excitation light is configured to illuminate only one site at a time.

21. The array reader according to either claim 18 or claim 19, wherein the excitation light is configured to illuminate an entire row or an entire column at any given instant.

22. The array reader according to claim 17, wherein the single light focusing element is disposed between the substrate and the TGBS.

23. The array reader according to claim 17, wherein the single light focusing element is disposed between the TGBS and the detector.

24. The array reader according to claim 17, wherein the sites comprise and array of nucleotides.

25. The array reader according to claim 17, wherein the TGBS is further configured to separate the non-collimated light received from the at least one sample into a $0^{th}$-order component which is received by a first set of light sensitive elements and a higher-order component which is received by a second set of light sensitive elements, the second set being spaced apart from the first set.

* * * * *